United States Patent

Volkert et al.

[11] Patent Number: 5,126,379
[45] Date of Patent: Jun. 30, 1992

[54] ESTERS CONTAINING BONDED FLUOROCARBON AND OXYPROPYLENEALKYLETHER GROUPS, EMULSIONS CONTAINING THESE ESTERS AND THEIR USE FOR THE PREPARATION OF CELLULAR PLASTICS BY POLYISOCYANATE POLYADDITION

[75] Inventors: Otto Volkert, Weisenheim; Werner Hinz, Frankenthal, both of Fed. Rep. of Germany

[73] Assignee: BASF Aktiengesellschaft, Ludwigshafen, Fed. Rep. of Germany

[21] Appl. No.: 629,296

[22] Filed: Dec. 18, 1990

[30] Foreign Application Priority Data

Dec. 19, 1989 [DE] Fed. Rep. of Germany ....... 3941871

[51] Int. Cl.$^5$ .............................. C08G 18/14
[52] U.S. Cl. ................... 521/110; 521/112; 521/114; 521/115; 252/182.22; 252/182.27
[58] Field of Search ............... 521/110, 112, 114, 115; 252/182.22, 182.23

[56] References Cited

U.S. PATENT DOCUMENTS

| | | | |
|---|---|---|---|
| 3,184,419 | 5/1965 | Merriman et al. | 260/2.5 |
| 3,398,182 | 8/1968 | Guenther et al. | 260/455 |
| 3,470,124 | 9/1969 | Eygen et al. | 260/29.6 |

FOREIGN PATENT DOCUMENTS

| | | |
|---|---|---|
| 0297822 | 1/1989 | European Pat. Off. |
| 1593635 | 1/1970 | Fed. Rep. of Germany |
| 2656423 | 6/1978 | Fed. Rep. of Germany |
| 1157320 | 9/1969 | United Kingdom |

Primary Examiner—Maurice J. Welsh
Attorney, Agent, or Firm—William G. Conger

[57] ABSTRACT

Novel esters containing bonded fluorocarbon and oxypropylenealkylether groups and of the formula $$Rf-CO(-OCH(CH_3)-CH_2-)_n OR$$

or $$Rf-NH-CO(-OCH(CH_3)-CH_2-)_n OR$$

where Rf is straight-chain or branched, partially fluorinated or perfluorinated alkyl of 2 to 10 carbon atoms, partially fluorinated or perfluorinated cycloalkyl of 4 to 8 carbon atoms,
perfluorophenyl or
perfluoroalkylphenyl where the perfluoroalkyl radical is of 1 to 6 carbon atoms,
R is straight-chain or branched alkyl of 1 to 4 carbon atoms and
n is an integer from 2 to 70, blowing agent-containing emulsions which have a long shelf life and contain at least one partially fluorinated or perfluorinated (cyclo)aliphatic hydrocarbon of 3 to 8 carbon atoms and/or sulfur hexafluoride, at least one unmodified or modified organic polyisocyanate or a relatively high molecular weight reactive hydrogen compound and at least one of the abovementioned carboxylic or carbamic esters, and the use of these emulsions for the preparation of cellular plastics by the polyisocyanate polyaddition method.

20 Claims, No Drawings

ESTERS CONTAINING BONDED FLUOROCARBON AND OXYPROPYLENEALKYLETHER GROUPS, EMULSIONS CONTAINING THESE ESTERS AND THEIR USE FOR THE PREPARATION OF CELLULAR PLASTICS BY POLYISOCYANATE POLYADDITION

The present invention relates to novel esters which contain bonded fluorocarbon and oxypropylenealkylether groups and are of the formula $$Rf-CO+OCH-CH_3 \atop | \atop CH_2 +_n OR$$

or $$Rf-NH-CO+OCH-CH_3 \atop | \atop CH_2 +_n OR$$

blowing agent-containing emulsions which have a long shelf life and contain
at least one partially fluorinated or perfluorinated (cyclo)aliphatic hydrocarbon of 3 to 8 carbon atoms and/or sulfur hexafluoride as the blowing agent,
at least one unmodified or modified organic polyisocyanate or a relatively high molecular weight reactive hydrogen compound as the coherent phase and
at least one of the abovementioned esters as an emulsifier,
and the use of these emulsions for the preparation of cellular plastics by the polyisocyanate polyaddition process.

Surfactants which contain bonded partially fluorinated and/or perfluorinated organic radicals which may be olefinically unsaturated and polyoxyalkylene groups as active groups are known.

According to DE-A-22 44 028 (GB-A-1 371 054), such a surfactant has the following three components: a terminal aliphatic perfluorinated carbon group of not less than 3 carbon atoms which is bonded via an ether bridge to a bifunctional polyoxyalkylene chain, which in turn possesses, as a terminal group, an oleophilic group having a terminal alkyl radical of 3 to 20 carbon atoms.

Perfluoroalkenyl or highly fluorinated alkyl radicals which are bonded via an ether bridge to, preferably, a polyoxyalkylene unit whose second hydroxyl group is etherified with an alkyl radical of 1 to 20 carbon atoms or with an alkylphenyl, an alkylnaphthyl, a perfluoroalkenyl or a highly fluorinated alkyl radical are described in DE-A-22 50 718 (GB-A-1 354 138). The disadvantage of these compounds is their difficult preparation, in particular the difficulty in bonding the fluorinated or perfluorinated alkyl radicals with the polyoxyalkylene group, which consists predominantly or completely of ethylene oxide units, via an ether bridge.

I 5 1058-105 relates to photosensitive, sheet-like materials and describes perfluorocarboxylic esters with polyoxyethylene and polyoxyethylene polyoxypropylene glycols, which have a free, reactive hydroxyl group as a terminal group.

Fluorine-containing esters for increasing the oil repellancy, fat repellancy or water repellancy in film-forming polymer materials are disclosed in GB-A 1 157 320. They are prepared, for example, by partially esterifying perfluorocarboxylic acids with polyhydric alcohols and then acetylating the remaining free hydroxyl groups, or by esterifying fluoroalkanols with polycarboxylic acids.

U.S. Pat. No. 4,289,892 and U.S. Pat. No.4,356,273 describe fluorine compounds which have reactive hydrogen atoms and possess an N-ethylsulfonamide group as a bridge member, and their use as foam stabilizers in polyurethane foams. In these bifunctional or polyfunctional fluorine compounds, the polyoxyalkylene radical consists of a polyoxyethylene polyoxypropylene radical having middle oxypropylene groups and terminal primary hydroxyl groups.

Perfluoroalkyl-substituted polyethers which have a similarly complicated structure and in which the perfluorinated alkyl radical is bonded to the polyether chain via an —SO$_2$—NR—CO—O— bridge are disclosed in DE-B-22 38 740 (U.S. Pat. No.3,906,027). The nonionic surfactants are used as foam stabilizers, in particular for polyurethane foams, as emulsifiers or as wetting agents.

The use of highly fluorinated or perfluorinated, low-boiling alkanes as blowing agents for polyurethane foams is also known, since these meet all important requirements with respect to nonflammability, toxicity, thermal conductivity and other physical properties (U.S. Pat. No. 3,184,419 and DE-A-38 24 354). Their poor solubility in the components for the preparation of the polyisocyanate polyadducts presents the only problems.

The mechanism for foam formation in the preparation of polyisocyanate polyadducts and the effect of surfactants based on siloxane/oxyalkylene copolymers on this reaction were described by B. Kanner et al. (J. of Cellular Plastics, January 1969, pages 32 to 39).

According to these and other publications, an essential requirement for the formation of cellular polyisocyanate polyadducts having a uniform cell structure and good mechanical properties is the homogeneous dissolution of the blowing agents, for example of the carbon dioxide and/or of the inert, low-boiling liquids, in the organic polyisocyanates and/or the compounds having reactive hydrogen atoms (Blowing Agents for Polyurethanes by L. M. Zwolinski in Rubber Age, July 1975, pages 50 to 55 and U.S. Pat. No. 3,184,419). If the blowing agents are not soluble in the abovementioned components, only coarse-pored or, in most cases, no foams at all are obtained.

According to U.S. Pat. No. 4,544,679, to reduce the stated disadvantage special polyol mixtures having increased fluorochlorohydrocarbon solubility are used and/or an attempt is made to obtain homogeneous solutions of blowing agents and the polyisocyanates and/or polyols by adding solubilizers in amounts which are sometimes considerable (K. Tanabe, I. Kamemura and S. Kozawa, 28th SPI Conf. 1984, pages 53 to 57).

It is an object of the present invention to replace the fluorochlorohydrocarbons which have been used to date and are known blowing agents for the preparation of cellular plastics by the polyisocyanate polyaddition process completely or partially by other environmentally friendly blowing agents. Highly fluorinated or perfluorinated, low-boiling hydrocarbons appear suitable for this purpose. However, the disadvantage of these compounds is that they are poorly soluble or essentially insoluble in the conventional components for the preparation of plastics containing urethane and/or isocyanurate groups. Another disadvantage is that the fluorinated compounds, probably owing to their very low surface tension, are in general very difficult to emulsify by means of known emulsifiers, so that such emulsions containing polyhydroxy compounds or organic polyisocyanates as the coherent phase have an insufficient shelf life. It was therefore initially necessary to develop effective and readily obtainable emulsifiers and suitable emulsions having a long shelf life and containing blowing agents.

We have found that this object is achieved, surprisingly, by novel emulsifiers which consist of a hydrophobic fluorocarbon group and a hydrophilic oxypropylenealkylether group, which are bonded to one another by a —CO—O— or —NH—CO—O— bridge member.

The present invention thus relates to esters which contain bonded fluorocarbon and oxypropylenealkylether groups and are of the formula

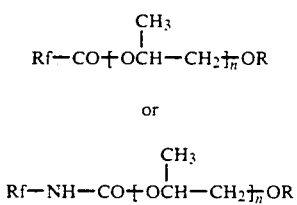

or

Rf—NH—CO+OCH—CH₂+ₙOR where
Rf is branched or, preferably, straight-chain, partially fluorinated or perfluorinated alkyl of 2 to 10 carbon atoms,
partially fluorinated or, preferably, perfluorinated cycloalkyl of 4 to 8, preferably 5 or 6, carbon atoms, perfluorophenyl or
perfluoroalkylphenyl where the perfluoroalkyl radical is of 1 to 6, preferably 1 to 3, carbon atoms,
R is branched or, preferably, straight-chain alkyl of 1 to 4, preferably 1 or 2, carbon atoms and
n is an integer from 2 to 70, preferably from 2 to 50, in particular from 5 to 25.

The present invention furthermore relates to emulsions which have a long shelf life, contain blowing agents and contain or, preferably, consist of
i) at least one partially fluorinated or perfluorinated, aliphatic and/or cycloaliphatic hydrocarbon of 3 to 8 carbon atoms, which is sparingly soluble or insoluble in (ii), and/or sulfur hexafluoride,
ii) at least one organic and/or modified organic polyisocyanate or at least one relatively high molecular weight compound having at least two reactive hydrogen atoms or a mixture of at least one relatively high molecular weight compound having at least two reactive hydrogen atoms and at least one low molecular weight chain extender and/or crosslinking agent
and
iii) at least one ester of the formula

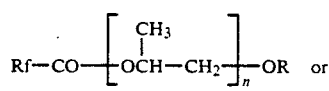

-continued

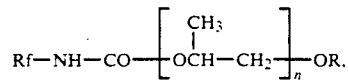

where Rf, R and n have the abovementioned meanings, and the use of these emulsions, which have a long shelf-life and contain blowing agents, for the preparation of cellular plastics by the polyisocyanate polyaddition process, preferably for the preparation of rigid polyurethane foams.

The novel carboxylic or carbamic esters which are suitable as emulsifiers and contain bonded fluorocarbon and oxypropylenealkylether groups are readily obtainable by reacting partially fluorinated or perfluorinated aliphatic or aromatic carboxylic acids or isocyanates with polyoxypropylene glycol monoalkyl ethers, possess, in comparison with the comb polymers likewise suitable but difficult to prepare and consisting of a polyacrylate main chain and side groups of a fluorinated organic radical and a polyoxyethylene or polyoxypropylene radical, a relatively low viscosity which facilitates meterability and processibility thereof, and form emulsions which, even with a high content, for example more than 40% by weight, of highly fluorinated or perfluorinated blowing agents in polyhydroxy compounds, preferably polyetherpolyols, are stable over several weeks and can be readily processed on conventional expansion units in this period.

Another advantage is that the emulsifying effect of the novel esters containing bonded fluorocarbon and oxypropylenealkylether groups can be surprisingly increased by the additional use of special silicone-based foam stabilizers and the quality of the emulsion can thus be improved.

As a result of the good emulsification of the suitable sparingly soluble or insoluble, partially fluorinated or perfluorinated, aliphatic and/or cycloaliphatic hydrocarbons and/or sulfur hexafluoride as blowing agents and their vaporization by the heat evolved in the polyisocyanate polyaddition reaction, surprisingly cellular plastics having a uniform fine cell structure are obtained.

Regarding the novel esters containing bonded fluorocarbon and oxypropylenealkylether groups, their preparation, the blowing agents suitable according to the invention for emulsion formation and the components for the preparation of the cellular polyisocyanate polyadducts, preferably the rigid foams containing urethane groups or urethane and isocyanurate groups, the following may be stated specifically.

As stated above, the novel esters containing bonded fluorocarbon and oxypropylene alkylether groups are of the structure

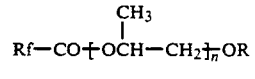

or

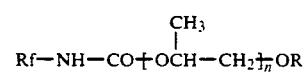

where
Rf is branched or, preferably, straight-chain, partially fluorinated alkyl of 2 to 10, preferably 3 to 6, carbon atoms, which is of, in particular, the formula $C_xF_{2x+1}-(CH_2)_y-$, where x is from 1 to 9, y is 1 or 2 and the sum of x and y is not more than 10, branched or, preferably, straight-chain, perfluorinated alkyl of 2 to 10, preferably 2 to 8, carbon atoms which is of, in particular, the formula $C_xF_{2x-1}$, where x is from 2 to 10, partially fluorinated or, preferably, perfluorinated cycloalkyl of 4 to 8, preferably 5 or 6, carbon atoms, for example perfluorinated cyclobutyl, cycloheptyl or cyclooctyl, or preferably a perfluorinated cyclopentyl or cyclohexyl group, perfluorinated phenyl or perfluoroalkylphenyl where the perfluoroalkyl group is of 1 to 6, preferably 1 to 3, carbon atoms, in particular one carbon atom, for example perfluorohexyl, perfluorobutyl, perfluoro-sec-butyl, perfluoropropyl, perfluoroisopropyl, perfluoroethyl or, in particular, perfluoromethylphenyl, R is branched or, preferably, straight-chain alkyl of 1 to 4, preferably 1 or 2, carbon atoms, for example n-butyl, sec-butyl, n-propyl, isopropyl, preferably ethyl, in particular methyl, and n is an integer from 2 to 70, preferably from 2 to 50, in particular from 5 to 25.

For emulsification, the carboxylic or carbamic esters containing bonded fluorocarbon and oxypropylenealkylether groups can be used individually or in the form of a mixture of two or more emulsifiers.

If the group Rf is only partially fluorinated, it should advantageously have a fluorine content of not less than 40, preferably not less than 70, % by weight, based on the weight of Rf.

The novel fluorocarbon-oxypropylenealkylether esters can be prepared, for example, by esterifying perfluorinated or partially fluorinated aliphatic carboxylic acids, perfluorinated aromatic carboxylic acids or perfluoroalkyl-substituted aromatic carboxylic acids or the corresponding carboxylic acid derivatives, preferably carbonyl chlorides, with polyoxypropylene glycol monoalkyl ethers having molecular weights of from 148 to 4134, preferably from 322 to 1524, which in turn are obtained by anionic polymerization of 1,2-propylene oxide with a straight-chain or branched alkanol of 1 to 4 carbon atoms, e.g. n-butanol, n-propanol, isopropanol, preferably ethanol or, in particular, methanol. In another variant of the process, the partially fluorinated or perfluorinated carboxylic acid derivatives are the corresponding alkyl esters of 1 to 3 carbon atoms or hydroxyalkyl esters of 2 to 4 carbon atoms, for example the corresponding methyl, ethyl, isopropyl or 2-hydroxyethyl esters, and are transesterified with the abovementioned polyoxypropylene glycol monoalkyl ethers. The addition reaction of the polyoxypropylene glycol monoalkyl ethers with partially fluorinated or perfluorinated, aliphatic or aromatic isocyanates proceeds particularly advantageously, so that this process is preferred for the preparation of the carbamic esters containing bonded fluorocarbon and oxypropylenealkylether groups.

Components which have proven particularly useful and are therefore preferably used are perfluorobutyric acid, in particular perfluorobutyryl chloride, perfluorohexylacetic acid, in particular perfluorohexylacetyl chloride, perfluorobenzoic acid, in particular perfluorobenzoyl chloride, and 3-trifluoromethylphenyl isocyanate, so that the group Rf consists of one of the groups $C_3F_7-$, $C_6F_{13}-CH_2-$, $C_6F_5-$ or $CF_3-C_6$-

$H_4-$, and particularly useful and therefore preferably used polyoxypropylene glycol monoalkyl ethers are polyoxypropylene glycol monomethyl ethers having a molecular weight of from 380 to 1366.

Emulsifiers which are therefore preferably used and are prepared by one of the abovementioned processes are esters or carbamic esters of the formulae

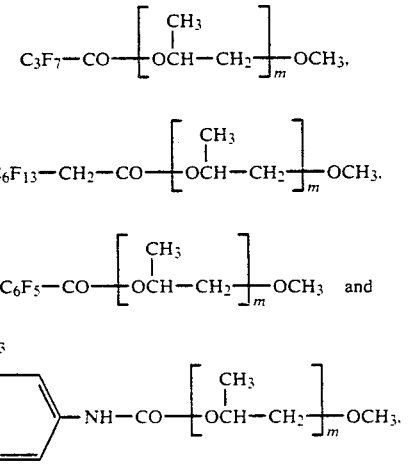

where m is from 6 to 23.

The novel carboxylic or carbamic esters containing bonded fluorocarbon and oxypropylenealkylether groups are used for the preparation of emulsions having a long shelf life and containing blowing agents, the said emulsions in turn being extremely useful for the preparation of cellular plastics, preferably rigid foams containing urethane groups or urethane and isocyanurate groups, by the polyisocyanate polyaddition process.

Cellular plastics of this type are prepared by the polyisocyanate polyaddition process, by reacting a) organic and/or modified organic polyisocyanates with b) at least one relatively high molecular weight compound having at least two reactive hydrogen atoms and, if required, c) low molecular weight chain extenders and/or crosslinking agents in the presence of d) blowing agents, e) catalysts and f) assistants and/or additives.

Components (a) to (f) which are advantageously used are the compounds described below, about which the following may be stated specifically:

a) Suitable organic polyisocyanates are the conventional aliphatic, cycloaliphatic, araliphatic and, preferably, aromatic polyvalent isocyanates.

Specific examples are alkylene diisocyanates where the alkylene radical is of 4 to 12 carbon atoms, such as dodecyl 1,12-diisocyanate, 2-ethyltetramethylene 1,4-diisocyanate, 2-methylpentamethylene 1,5-diisocyanate, tetramethylene 1,4-diisocyanate and, preferably, hexamethylene 1,6-diisocyanate; cycloaliphatic diisocyanates, such as cyclohexyl 1,3- and 1,4-diisocyanate and any mixtures of these isomers, 1-isocyanato-3,3,5-trimethyl-5-isocyanatomethylcyclohexane (isophorone diisocyanate), hexahydrotoluylene 2,4- and 2,6-diisocyanate and the corresponding isomer mixtures, dicyclohexylmethane 4,4'-, 2,2' and 2,4'-diisocyanate and the corresponding isomer mixtures and, preferably, aromatic di- and polyisocyanates, e.g. toluylene 2,4- and 2,6-diisocyanate and the corresponding isomer mixtures. diphenylmethane 4,4'-, 2,4'- and 2,2'-diisocyanate and the corresponding isomer mixtures, mixtures of diphenylmethane 4,4'- and 2,4'-diisocyanates, polyphenylpolymethylene polyisocyanates, mixtures of diphenylmethane 4,4'-, 2,4'- and 2,2'-diisocyanates and polyphenylpolymethylene polyisocyanates (crude MDI) and mixtures of crude MDI and toluylene diisocyanates The organic di- and polyisocyanates can be used individually or in the form of mixtures.

Frequently, modified polyvalent isocyanates, i.e. products which are obtained by chemical reaction of organic di- and/or polyisocyanates, are also used. Examples are di- and/or polyisocyanates containing ester, urea. biuret, allophanate, carbodiimide, isocyanurate, uretdione and/or urethane groups. Specific examples of suitable compounds are urethane-containing organic, preferably aromatic, polyisocyanates having NCO contents of from 33.6 to 15, preferably from 31 to 21, % by weight, based on the total weight, for example with low molecular weight diols, triols, dialkylene glycols, trialkylene glycols or polyoxyalkylene glycols having molecular weights of not more than 800, modified diphenylmethane 4,4'-diisocyanate or toluylene 2,4- or 2,6-diisocyanate, examples of di- or polyoxyalkylene glycols, which may be used individually or as mixtures, being diethylene, dipropylene, polyoxyethylene, polyoxypropylene and polyoxypropylene polyoxyethylene glycols. NCO-containing prepolymers having NCO contents of from 25 to 3.5, preferably from 21 to 14, % by weight, based on the total weight, are also suitable, the said prepolymers being prepared from the polyesterpolyols, or, preferably, polyetherpolyols described below and diphenylmethane 4,4'-diisocyanate, mixtures of diphenylmethane 2,4'- and 4,4'-diisocyanate, toluylene 2,4- and/or 2,6-diisocyanates or crude MDI. Liquid polyisocyanates containing carbodiimide groups and/or isocyanurate rings and having NCO contents of from 33.6 to 15, preferably from 31 to 21, % by weight, based on the total weight, for example those based on diphenylmethane 4,4'-, 2,4'- and/or 2,2'-diisocyanate and/or toluylene 2,4- and/or 2,6-diisocyanate, have also proven suitable.

The modified polyisocyanates may be mixed with one another or with unmodified organic polyisocyanates, for example diphenylmethane 2,4'-diisocyanate, diphenylmethane 4,4'-diisocyanate, crude MDI, toluylene 2,4-diisocyanate and/or toluylene 2,6-diisocyanate.

The following have proven particularly useful as organic polyisocyanates and are preferably used for the preparation of cellular elastomers: NCO-containing prepolymers having an NCO content of from 25 to 9% by weight, in particular those based on polyetherpolyols or polyesterpolyols and one or more diphenylmethane diisocyanate isomers, advantageously diphenylmethane 4,4'-diisocyanate, and/or modified urethane-containing organic polyisocyanates having an NCO content of from 33.6 to 15% by weight, in particular those based on diphenylmethane 4,4'-diisocyanate or diphenylmethane diisocyanate isomer mixtures; the following are preferably used for the preparation of flexible polyurethane foams: mixtures of toluylene 2,4- and 2,6-diisocyanates, mixtures of toluylene diisocyanates and crude MDI or, in particular, mixtures of the abovementioned prepolymers based on diphenylmethane diisocyanate isomers and crude MDI; and the following is preferably used for the preparation of rigid polyurethane or polyurethane/polyisocyanurate foams: crude MDI.

b) Advantageously used relatively high molecular weight compounds b) having at least two reactive hydrogen atoms are those having a functionality of from 2 to 8, preferably from 2 to 6, and a molecular weight of from 380 to 8,000, preferably from 1,200 to 6,000. For example, polyols selected from the group consisting of the polyetherpolyols, polyesterpolyols, polythioetherpolyols, polyesteramides, hydroxyl-containing polyacetals and hydroxyl-containing aliphatic polycarbonates or mixtures of at least two of the stated polyols have proven useful. Polyesterpolyols and/or polyetherpolyols are preferably used.

Suitable polyesterpolyols can be prepared, for example, from organic dicarboxylic acids of 2 to 12 carbon atoms, preferably aliphatic dicarboxylic acids of 4 to 6 carbon atoms, and polyhydric alcohols, preferably diols, of 2 to 12, preferably 2 to 6, carbon atoms. Examples of suitable dicarboxylic acids are succinic acid, glutaric acid, adipic acid, suberic acid, azelaic acid, sebacic acid, decanedicarboxylic acid, maleic acid, fumaric acid, phthalic acid, isophthalic acid and terephthalic acid. The dicarboxylic acids can be used both individually and as a mixture with one another. Instead of the free dicarboxylic acids, it is also possible to employ the corresponding dicarboxylic acid derivatives, for example dicarboxylic mono- and/or diesters of alcohols of 1 to 4 carbon atoms or dicarboxylic anhydrides. Dicarboxylic acid mixtures of succinic, glutaric and adipic acid in weight ratios of, for example, 20–35 : 35–50 : 20–32 parts by weight are preferably used, and in particular adipic acid. Examples of dihydric and polyhydric alcohols, in particular diols, are: ethanediol, diethylene glycol, 1,2- and 1,3-propanediol, dipropylene glycol, 1,4-butanediol, 1,5-pentanediol, 1,6-hexanediol, 1,10-decanediol, glycerol and trimethylolpropane. Ethanediol, diethylene glycol, 1,4-butanediol, 1,5-pentanediol, 1,6-hexanediol or mixtures of at least two of the stated diols, in particular mixtures of 1,4-butanediol, 1,5-pentanediol and 1,6-hexanediol, are preferably used. Polyesterpolyols of lactones, e.g. ε-caprolactone, or hydroxycarboxylic acids, e.g. ω-hydroxycaproic acid, can also be employed.

For the preparation of the polyesterpolyols, the organic, for example aromatic or, preferably, aliphatic, polycarboxylic acids and/or derivatives thereof and polyhydric alcohols can be subjected to polycondensation in the absence of a catalyst, or, preferably, in the presence of an esterification catalyst, advantageously in an atmosphere of inert gases, for example nitrogen, carbon monoxide, helium, argon, etc., in the melt at from 150° to 250° C., preferably from 180° to 220° C., under atmospheric or reduced pressure, to the desired acid number, which is advantageously less than 10, preferably less than 2. In a preferred embodiment, the esterification mixture is subjected to polycondensation at the abovementioned temperatures to an acid number of from 80 to 30, preferably from 40 to 30, under atmospheric pressure and subsequently under a pressure of less than 500 mbar, preferably from 50 to 150 mbar. Examples of suitable esterification catalysts are iron, cadmium, cobalt, lead, zinc, antimony, magnesium, titanium and tin catalysts in the form of metals, metal oxides or metal salts. However, the polycondensation can also be carried out in the liquid phase in the presence of diluents and/or entraining agents, for example benzene, toluene, xylene or chlorobenzene, for removal of the condensation water by azeotropic distillation.

For the preparation of the polyesterpolyols, the organic polycarboxylic acids and/or derivatives thereof and polyhydric alcohols are advantageously subjected to polycondensation in a molar ratio of from 1 : 1 to 1 : 1.8, preferably from 1 : 1.05 to 1 : 1.2.

The polyesterpolyols obtained preferably have a functionality of from 2 to 4, in particular 2 or 3, and a molecular weight of from 480 to 3,000, preferably from 1,200 to 3,000, in particular from 1,800 to 2,500.

However, polyols which are particularly used are polyetherpolyols which are prepared by known processes, for example by anionic polymerization using alkali metal hydroxides, such as sodium hydroxide or potassium hydroxide, or alkali metal alcoholates, such as sodium methylate, sodium ethylate, potassium ethylate or potassium isopropylate, as catalysts and with the addition of at least one initiator molecule which contains from 2 to 8, preferably from 2 to 6, bonded reactive hydrogen atoms, or by cationic polymerization using Lewis acids, such as antimony pentachloride, boron fluoride etherate, etc., or bleaching earth as catalysts, from one or more alkylene oxides where the alkylene radical is of 2 to 4 carbon atoms.

Examples of suitable alkylene oxides are tetrahydrofuran, 1,3-propylene oxide, 1,2- and 2,3-butylene oxide, styrene oxide and preferably ethylene oxide and 1,2-propylene oxide. The alkylene oxides can be used individually, alternately one after the other or as mixtures. Examples of suitable initiator molecules are water, organic dicarboxylic acids, such as succinic acid, adipic acid, phthalic acid and terephthalic acid, aliphatic and aromatic, N-mono-, N,N- or N,N'-dialkyl-substituted diamines where the alkyl radical is of 1 to 4 carbon atoms, such as unsubstituted or mono- or dialkyl-substituted ethylenediamine, diethylenetriamine, triethylenetetramine, 1,3-propylenediamine, 1,3- and 1,4-butylenediamine, 1,2-, 1,3-, 1,4-, 1,5- and 2,6-toluylenediamine, phenylenediamines, 2,3-, 2,4- and 2,6-hexamethylenediamine and 4,4'-, 2,4'- and 2,2'-diaminodiphenylmethane.

Other suitable initiator molecules are alkanolamines, dialkanolamines and/or trialkanolamines, such as ethanolamine, diethanolamine, N-methyl- and N-ethylethanolamine, N-methyl- and N-ethyldiethanolamine and triethanolamine, and ammonia. Polyhydric, in particular dihydric and/or trihydric, alcohols, such as ethanediol, 1,2- and 1,3-propanediol, diethylene glycol, dipropylene glycol, 1,4-butanediol, 1,6-hexanediol, glycerol, trimethylolpropane, pentaerythritol, sorbitol and sucrose, are preferably used.

The polyetherpolyols, preferably polyoxypropylenepolyols and polyoxypropylenepolyoxyethylenepolyols, have a functionality of, preferably, from 2 to 6, in particular from 2 to 4, and molecular weights of from 380 to 8,000, preferably from 400 to 6,000, in particular from 400 to 1,800, and suitable polyoxytetramethylene glycols have a molecular weight of not more than about 3,500.

Other suitable polyetherpolyols are polymer-modified polyetherpolyols, preferably graft polyetherpolyols, in particular those based on styrene and/or acrylonitrile, which are prepared by in situ polymerization of acrylonitrile, styrene or, preferably, mixtures of styrene and acrylonitrile, for example in a weight ratio of 90 : 10 to 10 : 90, preferably from 70 : 30 to 30 : 70, advantageously in the abovementioned polyetherpolyols, similarly to German Patents 1,111,394, 1,222,669 (U.S. Pat. Nos. 3,304,273, 3,383,351 and 3,523,093), 1,152,536 (British Patent 1,040,452) and 1,152,537 (British Patent 987,618), and polyetherpolyol dispersions which, as the disperse phase, usually contain from 1 to 50, preferably from 2 to 25, % by weight of, for example, polyureas, polyhydrazides, polyurethanes containing bonded tertiary amino groups and/or melamine and are described in, for example, EP-B-011 752 (U.S. Pat. No. 4,304,708), U.S. Pat. No. 4,374,209 and DE-A-32 31 497.

As in the case of the polyesterpolyols, the polyetherpolyols can also be used individually or in the form of mixtures. They may also be mixed with the graft polyetherpolyols or polyesterpolyols and the hydroxyl-containing polyesteramides, polyacetals and/or polycarbonates.

Examples of suitable hydroxyl-containing polyacetals are the compounds which can be prepared from glycols, such as diethylene glycol, triethylene glycol, 4,4'-dihydroxyethoxydiphenyldimethylmethane or hexanediol, and formaldehyde. Suitable polyacetals can also be prepared by polymerization of cyclic acetals.

Suitable hydroxyl-containing polycarbonates are those of the conventional type, which can be prepared, for example, by reacting diols, such as 1,3-propanediol, 1,4-butanediol and/or 1,6-hexanediol, diethylene glycol, triethylene glycol or tetraethylene glycol, with diaryl carbonates, e.g. diphenyl carbonate or phosgene.

The polyesteramides include, for example, the predominantly straight-chain condensates obtained from polybasic, saturated and/or unsaturated carboxylic acids or anhydrides thereof and polyhydric saturated and/or unsaturated amino alcohols or mixtures of polyhydric alcohols and amino alcohols and/or polyamines.

c) The polyisocyanate polyadducts and, preferably, foams containing urethane and isocyanurate groups can be prepared in the presence or absence of chain extenders and/or crosslinking agents. However, to modify the mechanical properties, for example the hardness, it may prove advantageous to add chain extenders, crosslinking agents or, if necessary, a mixture thereof. The chain extenders and/or crosslinking agents used are diols and/or triols having molecular weights of less than 400, preferably from 60 to 300. For example, aliphatic, cycloaliphatic and/or araliphatic diols of 2 to 14, preferably 4 to 10, carbon atoms, e.g. ethylene glycol, 1,3-propanediol, 1,10-decanediol, n-, m- and p-dihydroxycyclohexane, diethylene glycol, dipropylene glycol and, preferably, 1,4-butanediol, 1,6-hexanediol and bis-(2-hydroxyethyl)-hydroquinone, triols, such as 1,2,4- and 1,3,5-trihydroxycyclohexane, glycerol and trimethylolpropane, and low molecular weight hydroxyl-containing polyalkylene oxides based on ethylene oxide and/or 1,2-propylene oxide, and the abovementioned diols and/or triols are suitable as initiator molecules.

The chain extenders and/or crosslinking agents (c) can be used individually or as mixtures.

Where chain extenders, crosslinking agents or mixtures thereof are used, they are advantageously employed in amounts of from 2 to 60, preferably from 8 to 50, in particular from 10 to 40, % by weight, based on the weight of components (b) and (c).

d) Advantageously used blowing agents (d) or (i) are low-boiling fluorinated compounds which are sparingly soluble or insoluble in (a), (b), (c) or mixtures of (b) and (c) and which are selected from the group consisting of the partially fluorinated or perfluorinated hydrocarbons and sulfur hexafluoride. Partially or completely fluorinated, aliphatic or cycloaliphatic hydrocarbons of 3 to 8, preferably 3 to 6, carbon atoms which are gaseous or liquid at room temperature are particularly suitable, the gaseous fluoroalkanes being liquefied under superatmospheric pressure, for example under a pressure of not more than 100, preferably from 1 to 50, in particular from 2 to 10, bar and being emulsified in liquid form. Examples of aliphatic or cycloaliphatic perfluoroalkanes which are gaseous at room temperature are perfluoropropane, perfluorobutane and perfluorocyclobutane. Suitable aliphatic or cycloaliphatic perfluoroalkanes which are liquid at room temperature are, for example, perfluoropentane, perfluorohexane, perfluoroheptane and perfluorooctane or perfluorocyclopentane and perfluorocyclohexane. Advantageous partially fluorinated alkanes are hexafluoropropane and/or heptafluoropropane. Heptafluoropropane, perfluorocyclobutane, perfluoropentane and perfluorohexane have proven particularly useful and are therefore preferably used. The partially fluorinated or perfluorinated hydrocarbons stated by way of example and sulfur hexafluoride can be used individually or in the form of mixtures of two or more blowing agents.

The carboxylic and/or carbamic esters which are suitable as emulsifiers and contain bonded fluorocarbon and oxypropylenealkylether groups are advantageously used in an amount of from 0.01 to 6, preferably from 0.1 to 3.5, in particular from 0.5 to 2.0, parts by weight per 100 parts by weight of components (a) or (b) or of the mixture of (b) and (c).

The organic and/or modified organic polyisocyanates (a) and the relatively high molecular weight compounds having at least two reactive hydrogen atoms (b) are suitable for emulsifying the partially fluorinated hydrocarbons, perfluorinated hydrocarbons and/or sulfur hexafluoride which can be used as blowing agents (d), by means of the novel carboxylic or carbamic esters described above. Mixtures of (b) and low molecular weight chain extenders and/or crosslinking agents (c) are also suitable. The blowing agents (d), which are advantageously used in an amount of from 1 to 150, preferably from 1 to 70, in particular from 5 to 50, parts by weight per 100 parts by weight of (a) or (b), can be emulsified both in (a) and in (b) or in a mixture of (b) and (c) in order to form the emulsions having a long shelf life. For reasons relating to processing, it may prove advantageous to emulsify some of the blowing agent (d) in (a) and to emulsify the remainder of the blowing agent in (b) or in a mixture of (b) and (c), or, when different blowing agents (d) are used, one blowing agent (d) can be emulsified in (a) or (b) and the other blowing agent or blowing agents (d) can be emulsified in the other, remaining component.

When organic and/or modified organic polyisocyanates (a) are used as the other emulsion phase, aromatic polyisocyanates selected from the group consisting of toluylene 2,4- and 2,6-diisocyanate and mixtures of the stated isomers, diphenylmethane 4,4'-, 2,4'-, 2,2'-diisocyanate and mixtures of at least two of the stated isomers and mixtures of diphenylmethane diisocyanates and polyphenylpolymethylene polyisocyanates are preferably used. If the organic polyisocyanates are crystalline at room temperature, they are liquefied by mixing with liquid polyisocyanates and/or by suitable partial modification, for example the introduction of carbodiimide groups and/or urethane groups.

However, the relatively high molecular weight compounds having at least two reactive hydrogen atoms are preferably used as the other emulsion phase. Polyesterpolyols or mixtures thereof, having a functionality of 2 or 3 and a molecular weight of from 480 to 3,000, and polyetherpolyols or mixtures thereof, having a functionality of from 2 to 6 and a molecular weight of from 400 to 6,000, are particularly suitable, these advantageously being selected from the group consisting of the polyoxyethylenepolyols, polyoxypropy-lenepolyols, polyoxypropylene, polyoxyethylenepolyols and polyoxytetramethylene glycols or mixtures thereof.

The novel emulsions having a long shelf life and containing blowing agents thus contain or consist preferably of
i) from 1 to 150, preferably from 1 to 70, in particular from 5 to 50, parts by weight, based on 100 parts by weight of (ii) or (a), (b) or (b) and (c), of at least one low-boiling, partially fluorinated or perfluorinated, aliphatic and/or cycloaliphatic hydrocarbon of 3 to 8 carbon atoms which is sparingly soluble or insoluble in (ii) or (a), (b) or (b) and (c), and/or sulfur hexafluoride, as blowing agents (d) or (i),
ii) at least one organic and/or modified organic polyisocyanate (a) or at least one relatively high molecular weight compound having at least two reactive hydrogen atoms (b) or a mixture of (b) and low molecular weight chain extenders and/or crosslinking agents (c) and
iii) from 0.01 to 6.0, preferably from 0.1 to 3.5, parts by weight, based on 100 parts by weight of (ii) or (a), (b) or (b) and (e), of at least one ester of the formula

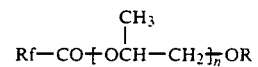

or

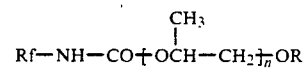

where Rf, R and n have the abovementioned meanings, and
iii) from 0 to 5.0, preferably from 0.1 to 3, in particular from 0.5 to 2, parts by weight, based on 100 parts by weight of (ii) or (a), (b) or (b) and (c), of at least one polysiloxane having polyether side chains, as a foam stabilizer.

For the preparation of the emulsions having a long shelf life and containing blowing agents, the components (a) or (b) or a mixture of (b) and (c) and the blowing agent (d) are thoroughly mixed in the presence of at least one of the novel carboxylic and/or carbamic esters containing bonded fluorocarbon and oxypropylenealkylether groups, at from 0° to 70° C., preferably from 20° to 40° C. Examples of suitable mixers for this purpose are static mixers, for example SMX from Sulzer (Switzerland), or dynamic mixers, for example Ultra-Turrax ® fron Hanke and Kunkel (FRG). If fluorinated hydrocarbons which are gaseous at room temperature are used for the preparation of the novel emulsions, these hydrocarbons are liquefied before or during the preparation of the emulsion, by the use of pressure of not more than 100 bar, so that, in particular, the blowing agents perfluoropropane, perfluorobutane and perfluorocyclobutane are present as a liquid phase in the emulsion under a pressure of not more than 100 bar.

In addition to the abovementioned blowing agents (d) or blowing agent emulsions, another suitable blowing agent is water, which reacts with the organic, unmodified or modified polyisocyanates (a) to form carbon dioxide and urea groups and thus affects the compressive strength of the end products. Since the amount of water present as a byproduct in the polyester- and polyetherpolyols is generally sufficient, the separate addition of water is often unnecessary. However, if water must additionally be incorporated in the polyurethane formulation, the water is usually used in amounts of from 0.05 to 2, preferably from 0.1 to 1, % by weight, based on the weight of the component (b).

The most advantageous amount of partially fluorinated and/or perfluorinated hydrocarbons and/or sulfur hexafluoride for the preparation of the cellular polyisocyanate polyadducts depends on the density required and on any amount of water used. In general, amounts of from 1 to 60, preferably from 5 to 40, in particular from 10 to 25, parts by weight of the blowing agent (d) per 100 parts by weight of components (a) to (c) or (a) and (b) give satisfactory results.

e) Compounds used in particular as catalysts (e) for the preparation of the cellular plastics by the polyisocyanate polyaddition method are those which greatly accelerate the reaction of the hydroxyl-containing compounds of component (b) and, where relevant, (c) with the organic, unmodified or modified polyisocyanates (a). Suitable compounds are organic metal compounds, preferably organic tin compounds, such as tin(II) salts of organic carboxylic acids, e.g. tin(II) acetate, tin(II) octoate, tin(II) ethylhexanoate and tin(II) laurate, and the dialkyltin(IV) salts of organic carboxylic acids, e.g. dibutyltin diacetate, dibutyltin dilaurate, dibutyltin maleate and dioctyltin diacetate. The organic metal compounds are used alone or, preferably, in combination with strong basic amines. Examples are amidines, such as 2,3-dimethyl-3,4,5,6-tetrahydropyrimidine, tertiary amines, such as triethylamine, tributylamine, dimethylbenzylamine, N-methyl-, N-ethyl- and N-cyclohexylmorpholine, N,N,N',N'-tetramethylethylenediamine, N,N,N',N'-tetramethylbutanediamine, pentamethyldiethylenetriamine, tetramethyldiaminoethylether,bis-(dimethylaminopropyl)-urea, dimethylpiperazine, 1,2-dimethylimidazole, 1-azabicyclo[3.3.0]octane and preferably 1,4-diazabicyclo2.2.2]octane, and alkanolamine compounds, such as triethanolamine, triisopropanolamine, N-methyl- and N-ethyldiethanolamine and dimethylethanolamine.

Other suitable catalysts are tris-(dialkylaminoalkyl)-s-hexahydrotriazines, in particular tris-(N,N-dimethylaminopropyl)-s-hexahydrotriazine, tetraalkylammonium hydroxides, such as tetramethylammonium hydroxide, alkali metal hydroxides, such as sodium hydroxide, and alkali metal alcoholates, such as sodium methylate and potassium isopropylate, and alkali metal salts of long-chain fatty acids which have 10 to 20 carbon atoms and may have OH side groups. Preferably from 0.001 to 5, in particular from 0.05 to 2, % by weight, based on the weight of component (b), of catalyst or catalyst combination are used.

f) Assistants and/or additives (f) may be incorporated in the reaction mixture for the preparation of the cellular plastics by the polyisocyanate polyaddition method. Examples are surfactants, foam stabilizers, cell regulators, fillers, dyes, pigments, flameproofing agents, hydrolysis stabilizers, and fungistatic and bacteriostatic substances.

Examples of suitable surfactants are compounds which are used for assisting homogenization of the starting materials and which may also be suitable for regulating the cell structure. Examples are emulsifiers, such as the sodium salts of castor oil sulfates or of fatty acids, and salts of fatty acids and amines, for example diethylammonium oleate, diethanolammonium stearate and diethanolammonium ricinoleate, salts of sulfonic acids, for example alkali metal or ammonium salts of dodecylbenzenesulfonic or dinaphthylmethanedisulfonic acid and ricinoleic acid; foam stabilizers, such as siloxane/oxyalkylene copolymers and other organopolysiloxanes, oxyethylated alkylphenols, oxyethylated fatty alcohols, liquid paraffins, castor oil esters and ricinoleic esters, Turkey red oil and peanut oil, and cell regulators, such as paraffins, fatty alcohols and dimethylpolysiloxanes. Foam stabilizers which have proven particularly useful and are therefore preferably used are polysiloxanes having polyether side chains, in particular those having a medium molecular weight and relatively high hydrophilicity, since, as described above, these make it possible to enhance the emulsifying effect of the novel esters containing bonded fluorocarbon and oxypropylenealkylether groups and to improve the foam properties. The fine, uniform cell structure of the rigid polyurethane foams produced in this manner is noteworthy. Such hydrophilic polysiloxanes having polyether side chains are commercial products and are available, for example, under the trade name Tegostab® B8406 and B8409 from Goldschmidt AG, Essen and under the code DC 190 and DC 193 from Dow Corning. The surfactants are usually used in amounts of from 0.01 to 5 parts by weight per 100 parts by weight of component (b).

Fillers, in particular reinforcing fillers, are the conventional organic and inorganic fillers, reinforcing agents, weighting materials, agents for improving the abrasion behavior in surface coatings, coating materials, etc. Specific examples are inorganic fillers, such as silicate minerals, e.g. sheet silicates, such as antigorite, serpentine, hornblendes, amphiboles, chrisotile, zeolites and talc; metal oxides, such as kaolin, aluminas, titanium oxides and iron oxides, metal salts, such as chalk and baryte, and inorganic pigments such as cadmium sulfide and zinc sulfide, as well as glass, etc. Kaolin (China clay), aluminum silicate and coprecipitates of barium sulfate and aluminum silicate, and natural and synthetic fibrous minerals, such as wollastonite, metal fibers and in particular glass fibers of various lengths, which may be sized, are preferably used. Examples of suitable organic fillers are carbon black, melamine, rosin, cyclopentadienyl resins, graft polymers, cellulose fibers and polyamide, polyacrylonitrile, polyurethane and polyester fibers based on aromatic and/or aliphatic dicarboxylic esters, and in particular carbon fibers.

The inorganic and organic fillers can be used individually or as mixtures and are advantageously incorporated in the reaction mixture in amounts of from 0.5 to 50, preferably from 1 to 40, % by weight, based on the weight of components (a) to (c), although the content of mats, nonwovens and woven fabrics of natural and synthetic fibers can reach values of up to 80% by weight.

Examples of suitable flameproofing agents are tricresyl phosphate, tris-2-chloroethyl phosphate, trischloropropyl phosphate and tris-2,3-dibromopropyl phosphate.

In addition to the abovementioned halogen-substituted phosphates, inorganic flameproofing agents, such as red phosphorus, aluminum oxide hydroxide, antimony trioxide, arsenic oxide, ammonium polyphosphate and calcium sulfate, or cyanuric acid derivatives, for example melamine, or mixtures of two or more flameproofing agents, such as ammonium polyphosphates and melamine, and, if required, corn starch can also be used for flameproofing the polyisocyanate polyadducts. In general, it has proven advantageous to use from 5 to 50, preferably from 5 to 25, parts by weight of the stated flameproofing agents per 100 parts by weight of component (b).

The technical literature, for example the monograph by J. H. Saunders and K. C. Frisch, High Polymers, Volume XVI, Polyurethanes, Parts 1 and 2, Interscience Publishers 1962 and 1964, or Kunststoff-Handbuch, Polyurethane, Volume VII, Hanser-Verlag, Munich, Vienna, 1st and 2nd Editions, 1966 and 1983, gives further information about the abovementioned other conventional assistants and additives.

For the preparation of the cellular urethane-containing plastics, the organic polyisocyanates (a), relatively high molecular weight compounds having at least two reactive hydrogen atoms (b) and, if required, chain extenders and/or crosslinking agents (c) are reacted in amounts such that the ratio of the number of equivalents of NCO groups of the polyisocyanates (a) to the sum of the reactive hydrogen atoms of components (b) and, where relevant, (c) is from 0.85 : 1 to 1.25 : 1, preferably from 0.95 : 1 to 1.15 : 1. If the cellular plastics contain, at least partially bonded isocyanurate groups, a ratio of NCO groups of the polyisocyanates (a) to the sum of the reactive hydrogen atoms of component (b) and, where relevant, (c) of from 1.5 : 1 to 60 : 1, preferably from 1.5 : 1 to 8 : 1, is usually used.

The cellular plastics of polyisocyanate polyadducts, such as cellular elastomers or, preferably, foams, in particular rigid foams, are advantageously produced by the one-shot method, for example using the reaction injection molding, high pressure or low pressure method in open or closed molds, for example thermostatable metallic molds. It has proven particularly advantageous to use the two-component method and to combine components (b), (d), (e) and, if required, (c) and (f) into component (a) and to use the organic polyisocyanates, modified polyisocyanates (a) or mixtures of the stated polyisocyanates and, if required, blowing agent (d) as component (B).

The starting components are mixed at from 15° to 90° C., preferably from 20° to 35° C., and introduced into the open mold or, if required, under superatmospheric pressure into the closed mold. As described above, mixing can be carried out mechanically by means of a stirrer or a spiral stirrer or under high pressure by the countercurrent injection method. The mold temperature is advantageously from 20° to 90° C., preferably from 30° to 60° C., in particular from 45° to 50° C.

The cellular elastomers prepared by the novel process have densities of about 0.76–1.0, preferably 0.9–1.0, g/cm³, and the densities of filler-containing products may reach higher values, for example up to 1.4 g/cm³ or more. Moldings obtained from such cellular elastomers are used in the automotive industry, for example as headrests, external parts, for example rear spoilers and bumpers, and interior trim, and as shoe soles.

The resilient and flexible, semi-rigid and rigid plastics prepared by the novel process and the corresponding integral foams have a density of from 0.02 to 0.75 g/cm³, the density of the foams being preferably from 0.025 to 0.24, in particular from 0.03 to 0.1, g/cm³, and the density of the integral foams being preferably from 0.08 to 0.75, in particular from 0.24 to 0.6, g/cm³. The foams and integral foams are used, for example, in the vehicle industry, for example the automotive, aircraft and shipbuilding industries and in the furniture and sports article industries as, for example, upholstery materials, housing parts, inner ski shoes, ski cores, etc. They are particularly suitable as insulation material in the building and refrigerator sectors. The novel emulsions which have a long shelf life and contain blowing agents are used for the preparation of cellular plastics, preferably foams containing urethane or urethane and isocyanurate groups, in particular rigid foams, and urethane-containing cellular elastomers by the polyisocyanate polyaddition method.

EXAMPLES a) Preparation of carboxylic or carbamic esters containing bonded fluorocarbon and oxypropylenealkylether groups

Example 1

33.6 parts by weight of polyoxypropylene glycol monomethyl ether having an OH number of 144 and prepared by anionic polyaddition of 1,2-propylene oxide with methanol were cooled to 0° C., and 20 parts by weight of perfluorobutyryl chloride were added in the course of 5 minutes with thorough stirring.

After a stirring time of 10 minutes, 13.6 parts by weight of pyridine were added dropwise to the reaction mixture in the course of 20 minutes. A colorless, crystalline precipitate was formed. The reaction mixture was then heated to 80° C. with further stirring and the reaction was completed in the course of 10 minutes at this temperature.

After the addition of 250 parts by weight of ice water and dilute hydrochloric acid, the reaction mixture was extracted by shaking with 100 parts by weight of ethyl acetate, the ethyl acetate fraction was washed twice with sodium bicarbonate solution and was dried, and the ethyl acetate was then distilled off at 40° C. under reduced pressure (about 100 mbar). The residue obtained comprised 54.4 parts by weight (93% by weight of theory) of the desired polyoxypropylene glycol monomethyl ether perfluorobutyrate in the form of a clear liquid having a fluorine content of 22.3% by weight. The theoretical fluorine content is 22.4% by weight.

Example 2

The procedure was carried out similarly to Example 1, except that the following starting materials and amounts were used: 32.3 parts by weight of polyoxypropylene glycol monomethyl ether having a hydroxyl number of 79 and prepared by anionic polyaddition of 1,2-propylene oxide with methanol,
18.0 parts by weight of perfluorohexylacetyl chloride ($C_6F_{13}$—$CH_2$—COCl) and
7.2 parts by weight of pyridine.

44.2 parts by weight (91% of theory) of the desired polyoxypropylene glycol monomethyl ether perfluorohexylacetate were obtained in the form of a reddish brown, slightly viscous liquid having a fluorine content of 22.2% by weight. The theoretical fluorine content is 23.0% by weight.

Example 3

The procedure was carried out similarly to Example 1, except that the following starting materials and amounts were used: 47.4 parts by weight of polyoxypropylene glycol monomethyl ether having a hydroxyl number of 79 and prepared by anionic polyaddition of 1,2-propylene oxide with methanol, 15.4 parts by weight of pentafluorobenzoyl chloride and
10.6 parts by weight of pyridine.

56.5 parts by weight (94% by weight of theory) of the desired polyoxypropylene glycol monomethyl ether pentafluorobenzoate were obtained in the form of a reddish brown liquid having a fluorine content of 10.1% by weight. The theoretical fluorine content is 10.5% by weight.

Example 4

18.7 parts by weight of 3-trifluoromethylphenyl isocyanate were added, while stirring under an atmosphere of dry nitrogen at 25° C. in the course of 20 minutes, to parts by weight of a polyoxypropylene glycol monomethyl ether having a hydroxyl number of 41 and prepared by anionic polyaddition of 1,2-propylene oxide with methanol.

The reaction mixture was then heated to 70° C. and the reaction was completed at this temperature by stirring for two hours. The polyoxypropylene glycol monomethyl ether N-(3-trifluoromethylphenyl)-carbamate was obtained in the form of a clear, yellowish liquid having a fluorine content of 3.6% by weight. The theoretical fluorine content is 3.64% by weight.

b) Preparation of emulsions having a long shelf life and containing blowing agents

Example 5

A mixture which consisted of 60 parts by weight of a polyoxypropylenepolyol having a hydroxyl number of 400 and prepared by anionic polyaddition of 1,2-propylene oxide with sucrose as the initiator molecule, 40 parts by weight of perfluorohexane and 0.5 part by weight of a polyoxypropylene glycol monomethyl ether perfluorobutyrate, prepared similarly to Example 1 from a polyoxypropylene glycol monomethyl ether having a hydroxyl number of 79 and perfluorobutyryl chloride, was mixed thoroughly with a high speed stirrer (2000 rpm) at 23° C. for 30 seconds.

An emulsion which did not contain any free, nonemulsified perfluorohexane and was still stable after a storage time of one week at room temperature was obtained.

Example 6

The procedure was similar to that of Example 5, except that in addition 1 part by weight of a foam stabilizer based on a hydrophilic polysiloxane having polyether side chains (Tegostab ® B8409 from Goldschmidt AG, Essen) was added to the mixture before emulsification.

An emulsion which, after storage for more than one week at room temperature, was stable and contained no free, separated, nonemulsified perfluorohexane was obtained.

Example 7

When the procedure described in Example 5 was followed but .5 part by weight of polyoxypropylene glycol monomethyl ether pentafluorobenzoate, prepared as described in Example 3, was used instead of the polyoxypropylene glycol monomethyl ether perfluorobutyrate, a stable emulsion which contained no free perfluorohexane and showed no signs of separation after a storage time of one week at room temperature was obtained.

Example 8

A mixture which consisted of 60 parts by weight of a polyoxypropylenepolyol having a hydroxyl number of 400 and prepared by anionic polyaddition of 1,2-propylene oxide with sucrose as the initiator molecule, 40 parts by weight of perfluorohexane, 1.0 part by weight of a hydrophilic polysiloxane having polyether side chains (Tegostab ® B8406 from Goldschmidt AG, Essen) and 0.5 part by weight of polyoxypropylene glycol monomethyl ether pentafluorobenzoate prepared as described in Example 3 was mixed thoroughly at 23° C. with a high speed stirrer (2000 rpm) for 30 seconds.

A stable emulsion which contained no free, nonemulsified perfluorohexane and, after storage for more than one week at room temperature, showed no signs of phase separation and contained no separated, free perfluorohexane was obtained.

COMPARATIVE EXPERIMENT I

A mixture which consisted of 60 parts by weight of a polyoxypropylenepolyol having a hydroxyl number of 400 and prepared by anionic polymerization of 1,2-propylene oxide with sucrose as the initiator molecule, 40 parts by weight of perfluorohexane and 1.0 part by weight of a hydrophilic polysiloxane having polyether side chains (Tegostab ® B8409 from Goldschmidt AG, Essen) was mixed thoroughly at 23° C. with a high speed stirrer (2000 rpm) for 30 seconds.

In the resulting emulsion, about 30 parts by weight (about 75% by weight) of the perfluorohexane used were present in emulsified form. The emulsion formed was separated off from the nonemulsified perfluorohexane and was stored at 23° C. In the course of 24 hours, the emulsion began to separate and perfluorohexane was deposited.

c) Preparation of a rigid polyurethane foam

Examples 9 TO 16

General preparation method

The carboxylic or carbamic esters mentioned below and containing bonded fluorocarbon and oxypropylenemethylether groups were first incorporated in the stated amounts in a mixture which consisted of 76.2 parts by weight of a polyoxypropylenepolyol having a hydroxyl number of 400 and prepared by anionic polyaddition of 1,2-propylene oxide with sucrose as the initiator molecule, 1.6 parts by weight of water and 2.1 parts by weight of N,N-dimethylcyclohexylamine and 2.0 parts by weight of a hydrophilic polysiloxane having polyether side chains (Tegostab ® B8409 from Goldschmidt AG, Essen), and 20 parts by weight of perfluorohexane were then emulsified in the resulting mixture with the aid of a high speed stirrer (2000 rpm) at 25° C. in the course of 30 seconds.

The resulting emulsions were mixed thoroughly at 23° C. with 109 parts by weight of a mixture of diphenylmethane diisocyanates and polyphenylpolymethylene polyisocyanates (crude MDI) having an NCO content of 31% by weight and the resulting reaction mixtures were introduced into an open, bucket-shaped vessel and allowed to expand freely there.

Very fine-celled rigid polyurethane foams having a density of 35 g/l and uniform cell structure, which cannot be achieved in the conventional expansion process using trichlorofluoromethane as the blowing agent, were obtained.

The resulting emulsions containing perfluorohexane as the blowing agent were stored at 23° C. and showed no signs of phase separation or separating out of perfluorohexane after 8 days.

After this time, they were again mixed with 109 parts by weight of crude MDI and allowed to expand by the method described.

The rigid polyurethane foams obtained showed no change in the cell structure.

thane foams having an even poorer cell structure were obtained.

Example 17

The procedure was carried out similarly to that in Example 10, except that, instead of perfluorohexane, 30 parts by weight of heptafluoropropane were used as the blowing agent.

A fine-celled rigid polyurethane foam having a density of 23 g/l was obtained.

Example 18

The procedure was carried out similarly to that in Example 11, except that, instead of perfluorohexane, 17 parts by weight of perfluoropentane were used as the blowing agent.

A very fine-celled rigid polyurethane foam having a density of 35 g/l was obtained.

Example 19

21 parts by weight of heptafluoropropane were emul-

TABLE

| Examples | Type Emulsifier | Amount [parts by wt.] | Foam structure |
|---|---|---|---|
| 9 | Carboxylic ester according to Example 1 | 1.64 | Excellent by fine-celled |
| 10 | Carboxylic ester prepared similarly to Example 1 from perfluorobutyryl chloride and a polyoxypropylene glycol monomethyl ether having a hydroxyl number of 79 | 1.64 | Very fine-celled |
| 11 | Carboxylic ester prepared similarly to Example 2 from perfluorohexylacetyl chloride and a polyoxypropylene glycol monomethyl ether having a hydroxyl number of 144 | 0.26 | Excellent by fine-celled |
| 12 | Carboxylic ester according to Example 2 | 0.26 | Very fine-celled |
| 13 | Carboxylic ester prepared similarly to Example 2 from perfluorohexylacetyl chloride and a polyoxypropylene glycol monomethyl ether having a hydroxyl number of 41 | 0.26 | Very fine-celled |
| 14 | Carboxylic ester according to Example 3 | 0.26 | Very fine-celled |
| 15 | Carbamic ester prepared similarly to Example 4 from 3-trifluoromethylphenyl isocyanate and a polyoxypropylene glycol monomethyl ether having a hydroxyl number of 144 | 0.26 | Very fine-celled |
| 16 | Carbamic ester prepared similarly to Example 4 from 3-trifluoromethylphenyl isocyanate and a polyoxypropylene glycol monomethyl ether having a hydroxyl number of 79 | 0.55 | Very fine-celled |

Comparative Experiment II 20 parts by weight of perfluorohexane were emulsified, by means of a high speed stirrer (2000 rpm) at 25° C. in the course of 30 seconds, in a mixture which consisted of 76.2 parts by weight of a polyoxypropylenepolyol having a hydroxyl number of 400 and prepared by anionic polyaddition of 1,2-propylene oxide with sucrose as the initiator molecule, 1.6 parts by weight of water, 2.1 parts by weight of N,N-dimethylcyclohexylamine and 2.0 parts by weight of a hydrophilic polysiloxane having polyether side chains (Tegostab® B8409 from Goldschmidt AG, Essen).

The resulting emulsion was immediately mixed thoroughly at 23° C. with crude MDI having an NCO content of 31% by weight and the reaction mixture obtained was introduced into an open bucket-shaped vessel and allowed to expand freely there.

A relatively coarse-celled rigid polyurethane foam having a density of 50 g/l was obtained.

When the foam stabilizer Tegostab® B8409 was replaced with other foam stabilizers based on siloxanes, for example Tegostab® B1903, B8406 or B8422 or DC190 or DC193 from Dow Corning, rigid polyuresified, at 23° C., while stirring, in a pressure-tight vessel, in a mixture which consisted of 58.4 parts by weight of a polyoxypropylenepolyol having a hydroxyl number of 490 and prepared using sorbitol as the initiator molecule, 8.0 parts by weight of glycerol, 11.1 parts by weight of dipropylene glycol, 1.9 parts by weight of diethanolamine, 14.0 parts by weight of β-trichloroethyl phosphate, 1.6 parts by weight of N,N-dimethylcyclohexylamine, 3.2 parts by weight of a polysiloxane having polyether side chain (Tegostab® B 8406 from Goldschmidt AG, Essen) and 1.8 parts by weight of polyoxypropylene glycol monomethyl ether perfluorobutyrate, prepared as described in Example 1. The stable emulsion was then mixed thoroughly at 23° C. with 155 parts by weight of a mixture of diphenylmethane diisocyanates and polyphenylpolymethylene polyisocyanates having an NCO content of 31% by weight and the reaction mixture was introduced into an open mold and allowed to expand freely there.

A fine-celled rigid polyurethane foam having a density of 50 g/l was obtained.

Example 20

2 parts by weight of sulfur hexafluoride were emulsified, at 23° C., while stirring, in a pressure-tight vessel, in a mixture which consisted of 70.4 parts by weight of a polyoxypropylene (80) polyoxyethylene (20) glycol having a hydroxyl number of 30 and prepared using 1,3-propanediol as the initiator, 17.5 parts by weight of a polyoxypropylene (80) polyoxyethylene (20) polyol having a hydroxyl number of 35 and prepared using glycerol as the initiator, 9.2 parts by weight of 1,4-butanediol, 0.1 part by weight of a polysiloxane having polyether side chains (DC 193 from Dow Corning), 1.8 parts by weight of a 25% strength solution of triethylenediamine in 1,4-butanediol, 0.02 part by weight of dibutyltin dilaurate and 1.0 part by weight of polyoxypropylene glycol monomethyl ether perfluorohexylacetate, prepared as described in Example 2. The resulting emulsion was then mixed thoroughly at 23° C. with 53 parts by weight of a urethane-containing polyisocyanate having an NCO content of 23% by weight and prepared by reacting diphenylmethane 4,4'-diisocyanate with a polyoxypropylene glycol having a molecular weight of 400 and the reaction mixture was introduced into an open mold and allowed to expand freely there.

A microcellular polyurethane foam having a density of 300 g/l was obtained.

We claim:

1. A blowing agent-containing emulsion which has a long shelf life and contains
   i) at least one partially fluorinated or perfluorinated aliphatic and/or cycloaliphatic hydrocarbon of 3 to carbon atoms which is sparingly soluble or insoluble in (ii), and/or sulfur hexafluoride,
   ii) at least one organic and/or modified organic polyisocyanate and at least one relatively high molecular weight compound having at least two reactive hydrogen atoms or a mixture of at least one relatively high molecular weight compound having at least two reactive hydrogen atoms and at least one low molecular weight chain extender and/or crosslinking agent and
   iii) at least one ester of the formula

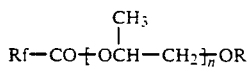

or

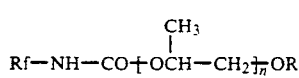

where Rf is straight-chain or branched, partially fluorinated or perfluorinated alkyl of 2 to 10 carbon atoms, partially fluorinated or perfluorinated cycloalkyl of 4 to 8 carbon atoms, perfluorophenyl or perfluoroalkylphenyl where the perfluoroalkyl radical is of 1 to 6 carbon atoms, R is straight-chain or branched alkyl of 1 to 4 carbon atoms and n is an integer from 2 to 70.

2. A blowing agent-containing emulsion which has a long shelf life and consists of
   i) from 1 to 150 parts by weight, per 100 parts by weight of (ii) of at least one partially fluorinated or perfluorinated aliphatic and/or cycloaliphatic hydrocarbon of 3 to 8 carbon atoms which is sparingly soluble or insoluble in (ii), and/or sulfur hexafluoride,
   ii) at least one relatively high molecular weight compound having at least two reactive hydrogen atoms or a mixture of at least one relatively high molecular weight compound having at least two reactive hydrogen atoms and at least one low molecular weight chain extender and/or crosslinking agent,
   iii) from 0.01 to 6.0 parts by weight, per 100 parts by weight of (ii), of at least one ester of the formula

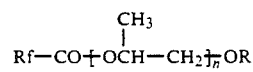

or

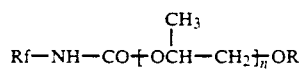

where Rf is straight-chain or branched, partially fluorinated or perfluorinated alkyl of 2 to 10 carbon atoms, partially fluorinated or perfluorinated cycloalkyl of 4 to 8 carbon atoms, perfluorophenyl or perfluoroalkylphenyl where the perfluoroalkyl radical is of 1 to 6 carbon atoms, R is straight-chain or branched alkyl of 1 to 4 carbon atoms and n is an integer from 2 to 70, and iiii) from 0 to 5.0 parts by weight, per 100 parts by weight of (ii), of at least one polysiloxane having polyether side chains as a foam stabilizer.

3. A blowing agent-containing emulsion having a long shelf life, as claimed in claim 1, wherein the fluorinated hydrocarbons (i) are selected from the group consisting of perfluoropentane, perfluorocyclopentane, perfluorohexane, perfluorocyclohexane, perfluoroheptane and perfluorooctane.

4. A blowing agent-containing emulsion having a long shelf life, as claimed in claim 1, wherein the fluorinated hydrocarbons (i) are selected from the group consisting of the gases perfluoropropane, perfluorobutane and perfluorocyclobutane, which are liquefied under a pressure of up to 100 bar.

5. A blowing agent-containing emulsion having a long shelf life, as claimed in claim 1, wherein the fluorinated hydrocarbons (i) consist of hexafluoropropane and/or heptafluoropropane.

6. A blowing agent-containing emulsion having a long shelf life, as claimed in claim 1, wherein the relatively high molecular weight compounds having at least two reactive hydrogen atoms consist of at least one polyesterpolyol having a functionality of 2 or and a molecular weight of from 480 to 3,000, or at least one polyetherpolyol having a functionality of 2 to and a molecular weight of from 380 to 8,000.

7. A blowing agent-containing emulsion having a long shelf life, as claimed in claim 1 or 6, wherein the ester (iii) is selected from compounds of the formulae

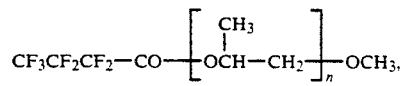

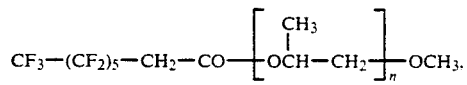

-continued

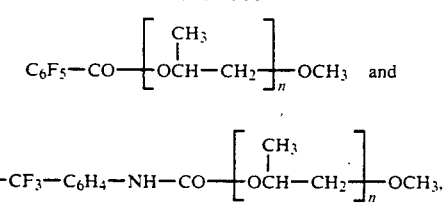

where n is from 6 to 24.

8. A blowing agent-containing emulsion which has a long shelf life and contains
   i) at least one partially fluorinated or perfluorinated aliphatic and/or cycloaliphatic hydrocarbon of 3 to 8 carbon atoms which is sparingly soluble or insoluble in (ii), and/or sulfur hexafluoride,
   ii) at least one organic and/or modified organic polyisocyanate and at least one relatively high molecular weight compound having at least two reactive hydrogen atoms or a mixture of at least one relatively high molecular weight compound having at least two reactive hydrogen atoms and at least one low molecular weight chain extender and/or cross-linking agent and
   iii) at least one ester of the formula

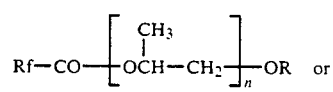

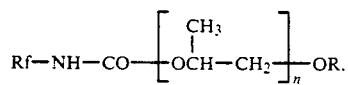

where Rf is straight-chain or branched, partially fluorinated or perfluorinated alkyl of 2 to 10 carbon atoms, partially fluorinated perfluorinated cycloalkyl of 4 to 8 carbon atoms, perfluorophenyl or perfluoroalkylphenyl where the perfluoroalkyl radical is of 1 to 6 carbon atoms, R is straight-chain or branched alkyl of 1 to 4 carbon atoms and n is an integer from 2 to 70, and
   iiii) alternatively, at least one polysiloxane having polyether side chains for the preparation of cellular plastics by the polyisocyanate polyaddition method.

9. A blowing agent-containing emulsion having a long shelf life, as claimed in claim 2, wherein the fluorinated hydrocarbons (i) are selected from the group consisting of perfluoropentane, perfluorocyclopentane, perfluorohexane, perfluorocyclohexane, perfluoroheptane and perfluorooctane.

10. A blowing agent-containing emulsion having a long shelf life, as claimed in claim 2, wherein the fluorinated hydrocarbons (i) are selected from the group consisting of the gases perfluoropropane, perfluorobutane and perfluorocyclobutane, which are liquefied under a pressure of up to 100 bar.

11. A blowing agent-containing emulsion having a long shelf life, as claimed in claim 2, wherein the fluorinated hydrocarbons (i) consist of hexafluoropropane and/or heptafluoropropane.

12. A blowing agent-containing emulsion having a long shelf life, as claimed in claim 2, wherein the relatively high molecular weight compounds having at least two reactive hydrogen atoms consist of at least one polyesterpolyol having a functionality of 2 or 3 and a molecular weight of from 480 to 3,000 or at least one polyetherpolyol having a functionality of 2 to 6 and a molecular weight of from 380 to 8,000.

13. A blowing agent-containing emulsion having a long shelf life, as claimed in claim 3, wherein the relatively high molecular weight compounds having at least two reactive hydrogen atoms consist of at least one polyesterpolyol having a functionality of 2 or 3 and a molecular weight of from 480 to 3,000 or at least one polyetherpolyol having a functionality of 2 to 6 and a molecular weight of from 380 to 8,000.

14. A blowing agent-containing emulsion having a long shelf life, as claimed in claim 4, wherein the relatively high molecular weight compounds having at least two reactive hydrogen atoms consist of at least one polyesterpolyol having a functionality of 2 or 3 and a molecular weight of from 480 to 3,000 or at least one polyetherpolyol having a functionality of 2 to 6 and a molecular weight of from 380 to 8,000.

15. A blowing agent-containing emulsion having a long shelf life, as claimed in claim 5, wherein the relatively high molecular weight compounds having at least two reactive hydrogen atoms consist of at least one polyesterpolyol having a functionality of 2 or 3 and a molecular weight of from 480 to 3,000 or at least one polyetherpolyol having a functionality of 2 to 6 and a molecular weight of from 380 to 8,000.

16. A blowing agent-containing emulsion having a long shelf life, as claimed in claim 2, wherein the ester (iii) is selected from compounds of the formulae

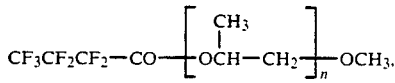

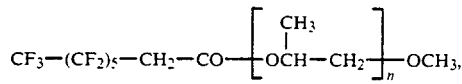

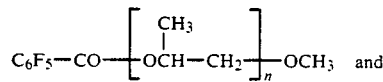

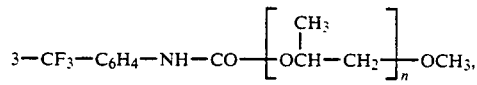

where n is from 6 to 24.

17. A blowing agent-containing emulsion having a long shelf life, as claimed in claim 3, wherein the ester (iii) is selected from compounds of the formulae

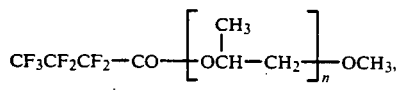

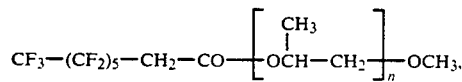

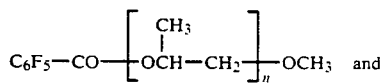

-continued

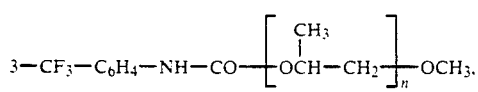

where n is from 6 to 24.

18. A blowing agent-containing emulsion having a long shelf life, as claimed in claim 4, wherein the ester (iii) is selected from compounds of the formulae

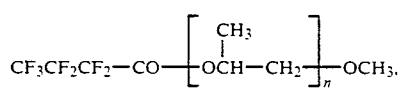

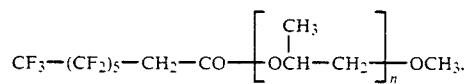

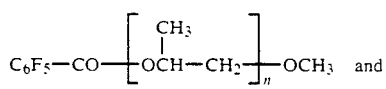 and

-continued

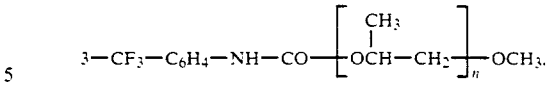

where n is from 6 to 24.

19. A blowing agent-containing emulsion having a long shelf life, as claimed in claim 5, wherein the ester (iii) is selected from compounds of the formulae

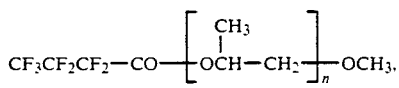

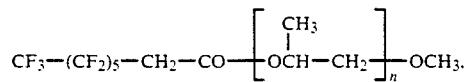

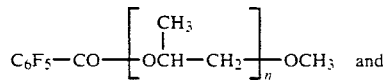 and

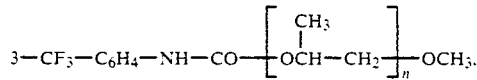

where n is from 6 to 24.

20. The blowing-agent-containing emulsion of claim 8, wherein said cellular plastic is a rigid polyurethane foam.

* * * * *